(12) United States Patent
Thomas et al.

(10) Patent No.: US 6,623,503 B1
(45) Date of Patent: Sep. 23, 2003

(54) DILATORS

(75) Inventors: Joan Thomas, Shifnal (GB); John Holden, Wolverhampton (GB); Peter Caudwell, Dudley (GB)

(73) Assignee: The Royal Wolverhampton Hospitals NHS Trust, Wolverhampton (GB)

( * ) Notice: Subject to any disclaimer, the term of this patent is extended or adjusted under 35 U.S.C. 154(b) by 0 days.

(21) Appl. No.: 09/937,293

(22) PCT Filed: Mar. 23, 2000

(86) PCT No.: PCT/GB00/01116
§ 371 (c)(1),
(2), (4) Date: Jan. 4, 2002

(87) PCT Pub. No.: WO00/56389
PCT Pub. Date: Sep. 28, 2000

(30) Foreign Application Priority Data

Mar. 24, 1999 (GB) .............................................. 9906668

(51) Int. Cl.[7] .............................................. A61M 29/00
(52) U.S. Cl. ...................................... 606/191; 606/197
(58) Field of Search ................................ 606/191, 198, 606/185, 193, 197, 199; 600/208

(56) References Cited

U.S. PATENT DOCUMENTS

| 876,775 | A | * | 1/1908 | Crittenden | .................. 606/191 |
| 1,327,786 | A | | 1/1920 | Stephan | |
| 1,877,766 | A | | 9/1932 | Kennedy | |
| 2,290,571 | A | | 7/1942 | Peyton | |
| 3,587,588 | A | | 6/1971 | Murr | |
| 4,263,914 | A | | 4/1981 | Pawlak | |
| 5,681,340 | A | * | 10/1997 | Veronikis | ..................... 606/191 |

FOREIGN PATENT DOCUMENTS

| DE | 369 320 | 2/1917 |
| DE | G 90 15 014.7 | 3/1991 |

* cited by examiner

Primary Examiner—Kevin T. Truong
(74) Attorney, Agent, or Firm—Foley Hoag LLP

(57) ABSTRACT

A first dilator (10) and second dilator (20) each comprise an elongate hollow member (11; 21) with a "closed" end (12; 22) and an "open" end (13; 23). The outer surface of the "closed" end (12; 22) is of uniform arcuate section and of generally hemispherical configuration. The "open" end (13) of the member (11) is provided with internal threading (16), while complementary external threading (24) is provided on the "open" end (23) of the member (21). In use, the first dilator (10) and second dilator (20) are joined together by engaging the threading (16; 24). A flange (25) provided on the second dilator (20) provides a continuously smooth outer surface.

21 Claims, 2 Drawing Sheets

DILATORS

This invention relates to dilators.

The present invention will be described hereinafter with particular reference to vaginal dilators. However, it is not to be construed as being limited thereto and dilators according to the present invention may, in appropriate circumstances, be suitable for use in connection with other orifices of the human or animal body, including artificial orifices which are responsive to dilation.

Vaginal dilators have been used for many years in medicine for a wide variety of applications including oncology, radiotherapy, gynaecology, obstetrics and sex therapy. In gynaecology, for example, sufferers from vaginismus may use a small dilator initially and gradually accustom themselves to its feel and size in an unpressured environment. As they become used to a small dilator they may then use a larger dilator until they reach an ability to tolerate their desired size.

A known type of dilator (sometimes called a "trainer" or "cone") comprises an elongate hollow cylinder having a "closed" end and an "open" end. The diameter of the cylinder progressively reduces towards the "closed" end so that the dilator has a tapering configuration. The "open" end of the cylinder is provided with one or more external circumferential lugs which are adapted, in use, to engage a handle. The handle is used for insertion and removal of the dilator.

Dilators are provided in varying lengths and diameters: a typical "set" of dilators generally consists of four or more dilators (e.g. of lengths 9 cm, 11 cm, 14 cm and 16 cm and respective diameters 20 mm, 25 mm, 30 mm and 35 mm). In dilators of the known type described in the immediately-preceding paragraph, the tapering configuration at the "closed" end can result in the smaller dilators in the "set" having a "closed" end which is almost "pointed", while the need to provide a universally-applicable handle results in the circumferential lugs at the "open" end being disproportionately large relative to the dimensions of the dilator. Both the aforesaid features of the known dilators can lead to aggravation of existing medical conditions and/or to physical injury. This is especially likely if a patient or surgeon, inserts the handle portion by mistake. Such mistakes are known to occur, especially under conditions of home use.

As dilators are frequently used by patients in their home environment it is important to provide a dilator which is intuitively easy and inherently safe to use. The dilator or set of dilators should be compact, attractive, and easy to clean.

We have devised dilators in which the disadvantages mentioned hereinabove are avoided.

Accordingly, in a first embodiment, the present invention provides a dilator comprising an elongate member having an "open" end and a "closed" end, and the inner surface of an aperture at the "open" end is so internally configured as to be adapted, in use, to engage a corresponding external configuration of a handle.

The present invention also provides, in a second embodiment, a dilator comprising an elongate member having an "open" end and a "closed"end, in which the outer surface of the member at the "closed" end is of arcuate longitudinal section and in which the outer surface of the member at the "open" end is so externally configured as to be adapted, in use, to engage the inner surface of the member of a dilator as described in the immediately-preceding paragraph.

Preferably, the elongate member is of substantially cylindrical configuration. Preferably, the member is hollow.

Again preferably, the handle has a section substantially similar to that of the dilator for at least a portion of its axial length where it engages the dilator. Preferably, the handle comprises another dilator.

Preferably, the outer surface of the member at the "closed" end is of arcuate longitudinal section.

The outer surface of the member at the "open" end is preferably also of arcuate longitudinal section. This may be achieved, for example, by moulding in a suitably-configured mould or by processes such as chamfering, bevelling or the like.

Preferably, at least the outer surface of the member at the "closed" end has a radius of curvature substantially equal to the outer radius of the member, whereby the outer surface of the member at the "closed" end is of generally hemispherical configuration.

In addition, the inner surface of the member at the "closed" end may have a radius of curvature substantially equal to the inner radius of the cylinder.

With reference to the dilator according to the first embodiment of the present invention, the internal configuration at the "open" end of the member preferably comprises threading.

With reference to the dilator according to the second embodiment of the present invention, the external configuration at the "open" end preferably comprises threading which is complementary to the threading on the internal surface of the dilator according to the first embodiment.

Preferably, the dilator according to the second embodiment is provided with an annular flange which is adapted, in use, to abut the outer surface of the dilators when the dilators are engaged together.

Thus, a first and a second dilator may be joined together so that a "double-ended" dilator is formed. Alternatively, one of the two dilators so joined together can constitute a handle for the insertion and removal of the other dilator.

The dilator may further comprise a passageway to allow fluid (e.g. air) communication between the "open" and "closed" ends of the dilator in use. Preferably this is a hole through the "closed" end of the dilator. Alternatively a groove may be formed in the external surface of the dilator for this purpose, to prevent a vacuum from forming when the dilator is in use.

The present invention also provides a set of dilators, the set comprising two or more first dilators and two or more corresponding second dilators, the dimensions of each member of the set being different.

For example, a set of dilators may comprise two first dilators of length 128 mm and 110 mm and respective outer diameters of 30 mm and 25 mm, together with two second dilators of length 130 mm and 111 mm and respective outer diameters of 20.5 mm and 13.7 mm.

The dilators may be made of any suitable plastics material which is non-toxic and non-allergenic and which can be provided with a substantially perfectly smooth outer surface.

The set of dilators may be stackable such that the smaller dilators fit substantially inside the larger dilators for ease of packing and transportation of the dilator set.

Preferably the dilator or set of dilators further comprises a lubricant. This may be of any suitable non-toxic and non-allergenic lubricating material. It may be an integral part of the dilators, dispensed by use of the dilator or applied by the user. Preferably, the lubricant is water based, particularly for applications in gynaecology or sex therapy, as this enables the user to continue existing condom use. In an alternative embodiment, the lubricant may be glycerine. This is particularly advantageous in radiotherapy applications and provides smooth lubrication which does not cause discomfort by drying out or becoming excessively sticky.

Advantageously, the dilator or set of dilators according to the present invention may be accompanied by training information in the use of the dilator. This may take the form of an information booklet, but any form of recorded information such as a videotape, audiotape, CD-ROM or instructions for accessing a relevant internet site may accompany the dilator or set of dilators. In a preferred embodiment the training information is specific to the particular application and the recording medium is coded appropriately.

Preferably the dilator or set of dilators is also accompanied by means for relaxing the dilator's user. This may take any form designed to engage or distract the user while the dilator is in use. It may take the form of music recorded on any appropriate medium, preferably on an audiotape.

Alternatively a stress ball or similar relaxing tactile stimulus could be provided.

This invention includes the use of a first and/or second dilator or set of dilators to dilate an orifice of the human body.

The present invention will be illustrated, merely by way of example, in the following description and with reference to the accompanying drawings.

In the drawings (wherein like numerals denote like parts):

Figure 1:
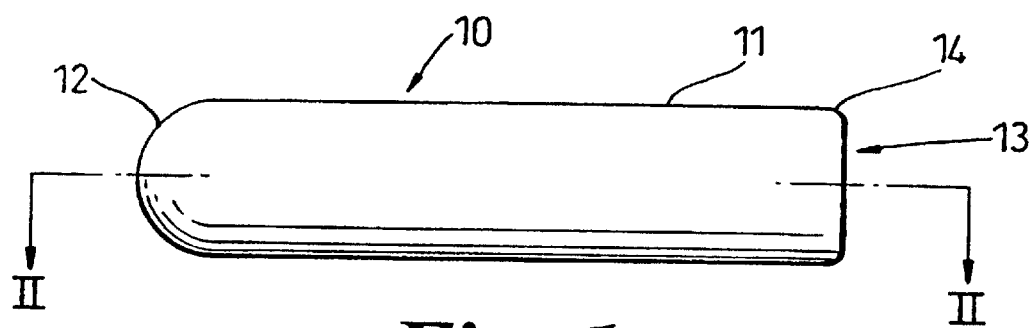
FIG. 1 is an elevation of a dilator according to the first embodiment of the present invention.
Figure 2:
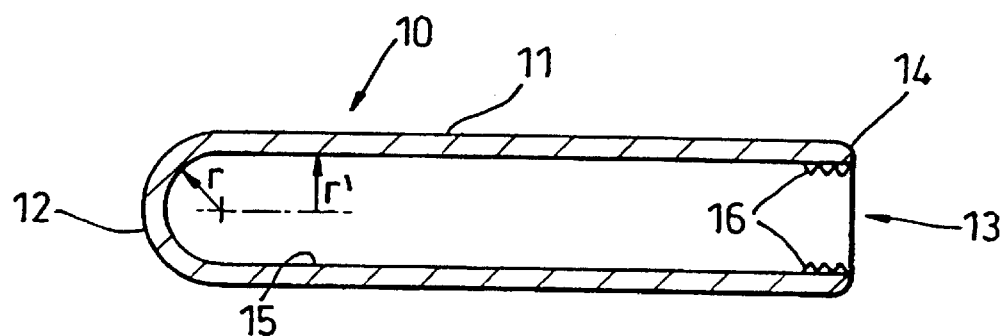
FIG. 2 is a section on line II—II of FIG. 1.

Referring to FIGS. 1 and 2, a first dilator 10 comprises an elongate hollow cylinder 11 with a "closed" end 12 and an "open" end 13.

The outer surface of the "closed" end 12 is of uniform arcuate section and of generally hemispherical configuration, the radius of curvature r of the inner surface being substantially equal to the internal radius r' of the cylinder 11.

At the "open" end 13, the outer surface 14 of the cylinder 11 is chamfered or bevelled so as to have an arcuate section.

Also at the "open" end 13, the inner surface 15 of the cylinder 11 is provided with threading 16.

Figure 3:
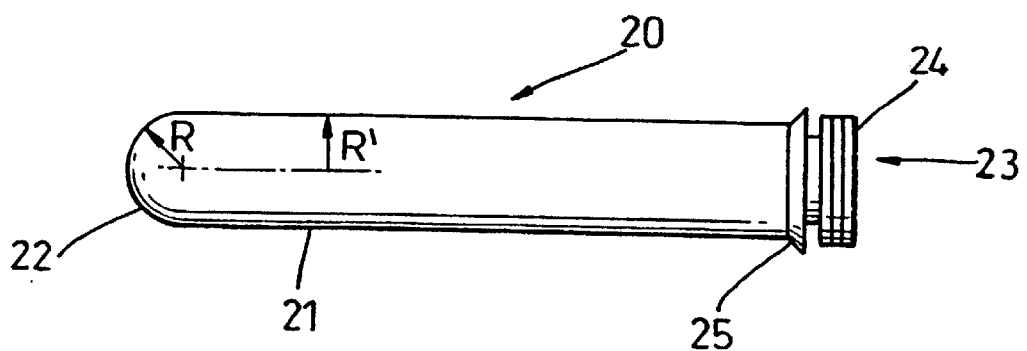
FIG. 3 is an elevation of a dilator according to the second embodiment of the present invention.

Referring to FIG. 3, a second dilator 20 comprises an elongate hollow cylinder 21 with a "closed" end 22 and an "open" end 23.

The outer surface of the "closed" end 22 is of uniform arcuate section and of generally hemispherical configuration, the radius of curvature R of the outer surface being substantially equal to the external radius R' of the cylinder 21.

At the "open" end 23, external threading 24 is provided. An annular flange 25 is provided adjacent the threading 24.

In use, first and second dilators are joined together by engagement of the external threading 24 of the second dilator and the internal threading 23 of the first dilator. The flange 25 abuts arcuate surface 14 so as to provide a continuously smooth outer surface.

The dilators are manufactured from polypropylene as this material displays the desired characteristics of stability and, light weight, although the dilators should have sufficient weight to be easily handled and manoeuvrable.

Figure 4:
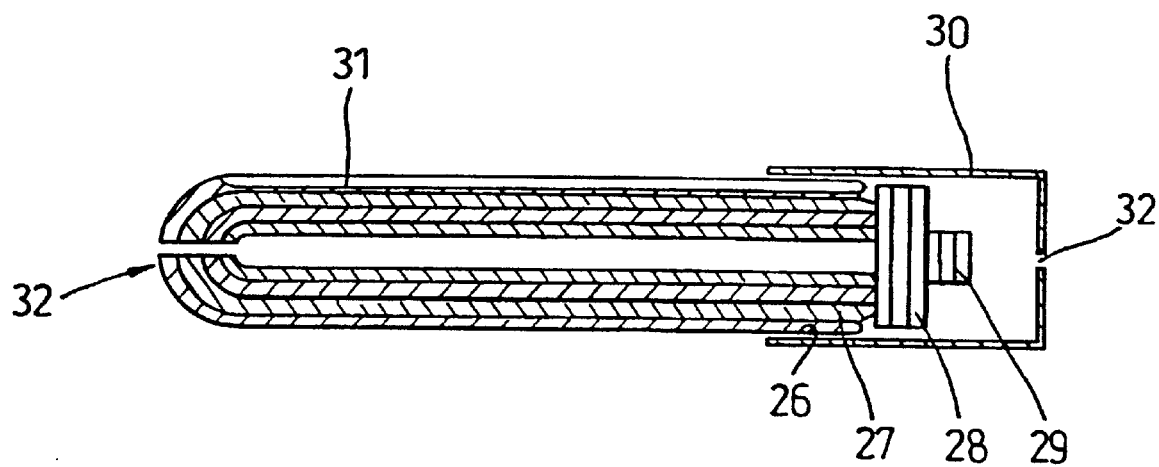
FIG. 4 is a longitudinal section of a fully assembled set of dilators according to the present invention.

FIG. 4 shows a set of dilators assembled into a form suitable for transportation and packing away. There are four dilators in this particular set: a large internally threaded dilator 26; a medium internally threaded dilator 27, a slightly smaller externally threaded dilator 28 and a small externally threaded dilator 29. The four dilators are sized to fit inside each other Russian-Doll style when packed away.

The set of dilators can be held in stacked form by means of a cap 30 which prevents dust or other contamination of the external threads.

A groove 31 of approximately one millimetre depth extends along the outer surface of each dilator. This groove 31 prevents the development of negative pressure inside the vagina when the dilator is being used, which can make the dilator difficult to extract. A hole 32 formed in the "closed" end of each dilator and in the cap 30 serves a similar purpose.

The set of dilators may be packaged, sold and/or used with appropriate lubrication. The type of lubrication depends on the application, with KY-Jelly, or another water based lubricant, being suitable for applications where the user is sexually active and wishes to continue existing condom use. Glycerine is particularly suitable for radiotherapy applications where the user will have been rendered sterile by the radiotherapy treatment, and also for when the user is not sexually active. It forms a smooth lubricant layer which does not dry out quickly. Moreover, some couples may wish to use dilation as part of their sexual relationship.

The dilators may also be accompanied by an information training leaflet, the content of which depends on the medical application, and the colour of which is coded accordingly. Finally, an audiotape containing relaxing music may accompany the set to enable the user to achieve a suitable frame of mind with appropriately relaxed muscles.

These dilators and ancillary equipment enable treatment of a variety of conditions under comfortable and safe conditions. They are easy to handle, position and cannot be wrongly inserted by mistake. It is easy to appreciate the many varieties and improvements of the present invention which should be understood to be limited in scope only by the appended claims.

What is claimed is:

1. A set of dilators, said set comprising
   at least a first dilator and a second dilator each comprising
      a first elongate member, said first elongate member having an "open" end and a "closed" end, an inner surface of said first elongate member at the "open" end being so internally configured as to be adapted, in use, to engage a corresponding external configuration of a handle for the dilator; and
   at least a third dilator and a fourth dilator each comprising
      a second elongate member, said second elongate member having an "open" end and a "closed" end, an outer surface of the second elongate member at the "closed" end being of arcuate longitudinal section and the outer surface of the second elongate member at the "open" end being so externally configured as to be adapted, in use, to engage the inner surface of the first elongate member of a dilator of the first dilator or the second dilator,
   wherein the dimensions of each elongate member of said set being different.

2. The Set of dilators of claim 1, wherein said first elongate member is of substantially cylindrical configuration.

3. The Set of dilators of claim 1, wherein said first elongate member is hollow.

4. The set of dilators of claim 1, wherein the second elongate member forms the handle.

5. The set of dilators of claim 1, wherein said outer surface of the second elongate member at said "closed" end is of arcuate longitudinal section.

6. The set of dilators of claim 5, wherein said arcuate longitudinal section of the outer surface is uniform.

7. The set of dilators of claim 1, wherein an outer surface of the first elongate member at the "open" end is of arcuate longitudinal section.

8. The set of dilators of claim 7, wherein said arcuate longitudinal section of the outer surface is uniform.

9. The set of dilators of claim 1, wherein said outer surface of the second elongate member at the "closed" end has a radius of curvature (R) substantially equal to the outer radius (R') of the second elongate member, whereby the outer surface of the second elongate member at the "closed" end is of generally hemispherical configuration.

10. The set of dilators of claim 1, wherein said inner surface of the first elongate member at the "closed" end has a radius of curvature (r) substantially equal to the inner radius (r') of the first elongate member.

11. The set of dilators of claim 1, wherein said internal configuration at the "open" end of the first elongate member comprises threading.

12. The set of dilators of claim 11, wherein said external configuration at the "open" end of the second elongate member comprises threading which is complementary to the threading at the "open" end of the first elongate member.

13. The set of dilators of claim 1, said second elongate member further having an annular flange which is adapted, in use, to abut an outer surface of said first elongate member when the elongate members are engaged together.

14. The set of dilators of claim 1, said dilators having been manufactured by molding.

15. The set of dilators of claim 14, said dilators having been made from a plastics material.

16. The set of dilators of claim 1, said dilators having been manufactured by machining.

17. The set of dilators of claim 16, said dilators having been made from a plastics material.

18. The set of dilators of claim 1, wherein the outer surface of said second elongate member is substantially perfectly smooth.

19. The set of dilators of claim 1, said dilators further comprising a passageway to allow fluid communication between the "open" end and the "closed" end of the first elongate member in use.

20. The set of dilators according to claim 1, wherein said dilators are stackable.

21. The set of dilators according to claim 1, said set further including a lubricant.

* * * * *